United States Patent
Joo et al.

(10) Patent No.: US 6,552,229 B1
(45) Date of Patent: Apr. 22, 2003

(54) METHOD FOR PREPARING 4-NITROSO-SUBSTITUTED AROMATIC AMINE

(75) Inventors: Young-J Joo, Daejeon (KR); Jin-Eok Kim, Daejeon (KR); Jeong-Im Won, Daejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 10/209,263

(22) Filed: Jul. 31, 2002

(30) Foreign Application Priority Data

Oct. 31, 2001 (KR) .......................................... 2001-67382

(51) Int. Cl.⁷ ............................................ C07C 209/00
(52) U.S. Cl. ....................................... 564/414; 564/441
(58) Field of Search .................................. 564/414, 441

(56) References Cited

U.S. PATENT DOCUMENTS

| | | | |
|---|---|---|---|
| 3,338,966 A | 8/1967 | Snyder | |
| 5,117,063 A | 5/1992 | Stern et al. | |
| 5,331,099 A | 7/1994 | Stern et al. | |
| 5,436,371 A | 7/1995 | Stern et al. | |
| 6,245,943 B1 | 6/2001 | Joo et al. | |

FOREIGN PATENT DOCUMENTS

| | | |
|---|---|---|
| EP | 0695739 A1 | 2/1996 |
| WO | WO 93/24447 | 12/1993 |

OTHER PUBLICATIONS

Williams, The Mechanism of the Fischer–Hepp Rearrangement of Atomatic N–Nitroso–Amines, Tetrahedron; vol. 31, pp 1343–1349; Pergamon Press 1975; Great Britain.

Willenz p–Nitrosoaniline, J. Chem. Soc., 1955, p 2049.

Stern, et al., Animation of Nitrobenzene via Nucleophilic Aromatic Substitution for Hydrogen: Direct Formation of Aromatic Amide Bonds, J.Org. Chem., 1993, vol. 58, p. 6883–6888.

Stern, et al., Direct Coupling of Aniline and Nitrobenzene: A New Example of Nucleophilic Aromatic Substitution for Hydrogen, J. Am. Chem. Soc., 1992, vol. 114, p. 9237–9238.

*Primary Examiner*—Samuel Barts
(74) *Attorney, Agent, or Firm*—Davidson, Davidson & Kappel, LLC

(57) ABSTRACT

Disclosed is a method for preparing a 4-nitroso-substituted aromatic amine that includes contacting an amide compound with a nitroaromatic compound in the presence of a base and a solvent to directly prepare 4-nitroso-substituted aromatic amine as a main product and 4-nitro-substituted aromatic amine as a by-product without producing 4-nitroso- or 4-nitro-substituted amide as an intermediate.

10 Claims, No Drawings

METHOD FOR PREPARING 4-NITROSO-SUBSTITUTED AROMATIC AMINE

BACKGROUND OF THE INVENTION

1. Field of the Invention

The present invention relates to a method for preparing a 4-nitroso-substituted aromatic amine and, more particularly, to a method for selectively preparing a 4-nitroso-substituted aromatic amine by contacting an amide compound with a nitroaromatic compound in the presence of a base in a polar organic solvent.

2. Related Prior Art

In general, 4-nitroso-substituted aromatic amines partly used as an intermediate of dye or hair dyes and a light stabilizer have not been studied much with regard to their applications because of their complicated method of preparation. Among the 4-nitroso-substituted aromatic amines, 4-nitrosoaniline is used as an intermediate of dye or hair dyes and usually reduced to a raw material for preparation of p-phenylenediamine (U.S. Pat. No. 6,245,943).

Conventionally, 4-nitrosoaniline is prepared by contacting aniline with sodium nitrite (NaNO2) to produce N-nitrosoaniline and then subjecting the N-nitrosoaniline to Fischer-Hepp rearrangement in acidic condition (Tetrahedron, 1975, 31, 1343–9), or by contacting p-nitrosophenol with ammonia or ammonium chloride (NH4Cl) (U.S. Pat. No. 3,338,966; and J. Chem. Soc., 1955, 2049).

The former method involves denitrosation during the Fischer-Hepp rearrangement step to produce waste containing lots of nitroso (NO) compounds destructive to the environment. The latter one using 4-nitrosophenol has a problem in regard to an excessively low yield of 4-nitrosoaniline, which problem causes the difficulty in mass production of 4-nitrosoaniline and hence the limited uses of 4-nitrosoaniline.

Recently, there has been developed a method for selectively preparing nitroaniline by nucleophilic aromatic substitution of hydrogen (NASH). For example, benzamide or benzonitrile is contacted with nitrobenzene in the presence of an organic base, tetramethylammonium hydroxide (hereinafter, referred to as "TMA(OH)") to prepare N-(4-nitrophenyl)benzamide as an intermediate, which is isolated and decomposed into 4-nitroaniline and benzoic acid (or benzamide) by addition of water (or ammonia) (J. Org. Chem., 1993, 58(24), 6883–8; U.S. Pat. Nos. 5,436,371 and 5,331,099; and International Publication No. WO 93/24447). This method is a direct amination with nitrobenzene using NASH that produces 4-nitroaniline, also called "para-nitroaniline" in two steps.

Other similar methods for preparing substituted nitroaromatic compounds through direct amination using NASH reaction are also known (European Publication No. EP 695739; and Japanese Publication No. JP 8040994).

In addition, another known method involves contacting an aliphatic amide, isobutyramide with benzene to produce N-(4-nitrophenyl)butyramide as an intermediate (U.S. Pat. No. 5,331,099). In this method, N-(4-nitrophenyl)butyramide is decomposed with ammonia or subjected to hydrolysis to yield 4-nitroaniline.

As is well known, the direct amination of an amide compound with a nitroaromatic compound using NASH reaction produces an intermediate of 4-nitro-substituted aromatic amine, which is decomposed with water or ammonia into 4-nitro-substituted aromatic amine. But there is no related document on the production of 4-nitroso-substituted aromatic amine.

However, 4-nitroso- or 4-nitro-substituted aromatic amine can also be produced through direct amination that involves contacting aniline as an aromatic amine other than an amide compound with nitrobenzene for NASH reaction (J. Am. Chem. Soc., 1992, 114(23), 9237–8; and U.S. Pat. No. 5,117,063).

As stated above, the conventional method involving the reaction between an amide compound and nitrobenzene is a two-step process that first produces an intermediate of 4-nitro-substituted aromatic amide and then hydrolyzes the intermediate with ammonia or water into the final product, 4-nitro-substituted aromatic amine. In this method, the process for production of the 4-nitroso-substituted aromatic amine is unknown.

DETAILED DESCRIPTION OF THE INVENTION

Accordingly, the inventors of the present invention have explored a one-step method for preparing a 4-nitroso-substituted aromatic amine using NASH reaction by contacting an amide compound with a nitroaromatic compound in an appropriate condition without producing 4-nitroso- or 4-nitro-substituted amide as an intermediate.

It is therefore an object of the present invention to provide a method for preparing a 4-nitroso-substituted aromatic amine and 4-nitro-substituted aromatic amine with high selectivity and high yield in one step of contacting a nitroaromatic compound with an amide compound in the presence of a base.

To achieve the object of the present invention, there is provided a method for preparing a 4-nitroso-substituted aromatic amine that includes contacting a nitroaromatic compound represented by the following formula 3 with an amide compound represented by the following formula 4 in the presence of a base to directly prepare a 4-nitroso-substituted aromatic amine represented by the following formula 1 as a main product and a 4-nitro-substituted aromatic amine as a by-product in one step:

Formula 1 wherein Ar is a $C_4$ to $C_{16}$ aromatic group having one or at least one ring and containing one or two hetero atoms of N, O or S; X is a halogen atom, a cyano group, a $C_1$ to $C_4$ alkyl group, a halongenated $C_1$ to $C_4$ alkyl group, a $C_1$ to $C_4$ alkoxy group, a $C_1$ to $C_4$ halogenated alkoxy group, a $C_1$ to $C_4$ alkylsulfonyl group, or a $C_1$ to $C_4$ alkylnitro group; and n is an integer of 0 to 3, wherein X is different from one another when n is greater than 1;

Formula 2 wherein Ar, X and n are as defined above;

Formula 3

wherein Ar, X and n are as defined above; and

Formula 4

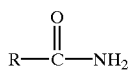

wherein R is a hydrogen atom, a $C_1$ to $C_8$ alkyl group, a $C_2$ to $C_8$ alkenyl group, or a $C_3$ to $C_7$ cycloalkyl group, which substituent may be replaced with 1 to 3 halogen atoms, $C_1$ to $C_4$ alkyl groups, amino groups or $C_1$ to $C_4$ alkoxy groups.

The 4-nitroso- and 4-nitro-substituted aromatic amines thus obtained are susceptible to normal hydrogenation to yield a diamine-substituted aromatic compound.

The present invention is directed to a method for preparing a 4-nitroso-substituted aromatic amine with a very high selectivity from an amide compound and a nitroaromatic compound in the presence of an inorganic or organic base in a polar organic solvent.

In the preparation method of the present invention, the nitroso-substituted aromatic amine prepared from the nitroaromatic compound of the formula 3 and the amide compound of the formula 4 is represented by the formula 1 and produced together with a small amount of a nitro-substituted aromatic amine (formula 2). The oxygen and air atmosphere may suppress production of azoxybenzene as a by-product and therefore enable selective production of the nitroso-substituted aromatic amine.

More specifically, examples of the nitroaromatic compound of the formula 3 suitable as a starting material may include nitrobenzene, 3-nitroanisole, 3-nitrotoluene, 2-nitroanisole, 2-nitrotoluene, m-chloronitrobenzene, 2,3,4-nitropyridine, and 5,6,7-nitroquinoline.

Specific examples of the amide compound of the formula 4 being contacted with the nitroaromatic compound may include urea, acetamide, formamide, biuret, phenylurea, and isobutyramide.

The base available in the present invention includes both inorganic and organic bases. Specific examples of the inorganic base may include alkali metal hydroxides, alkali metal amides, alkali metal alkoxides, and alkali metal hydrides. Among these inorganic bases, the preferred alkali metal hydroxides are sodium hydroxide (NaOH), potassium hydroxide (KOH), and potassium tert-butoxide (t-BuOK), which are preferably in the form of powder or fine particles.

Specific examples of the organic base may include tetraalkylammonium hydroxides, and TMA(OH) is particularly preferred.

The use of a phase transfer catalyst with the inorganic base may increase the reactivity Specific examples of the phase transfer catalyst may include crown ethers and tetraalkylammonium salts. Among these catalysts, 18-crown-6 and tetramethylammonium chloride (hereinafter, referred to as "TMA(Cl)") are particularly preferred.

The mole ratio of the base to the amide compound of the formula 4 is 1:0.5 to 1:10, preferably 1:1 to 1:6.

Specific examples of the solvent may include polar organic solvents, such as dimethylsulfoxide (hereinafter, referred to as "DMSO"), dimethylformamide (hereinafter, referred to as "DMF"), N-methylpyrrolidinone (hereinafter, referred to as "NMP"), pyridine, dioxane, and tetrahydrofurane (hereinafter, referred to as "THF"). These solvents may be used alone or in combination. Among these solvents, DMSO is most preferred. Alternatively, the amide compound or the nitroaromatic compound itself can be used as a solvent.

The weight ratio of the solvent to the amide compound of the formula 4 is 1:0.5 to 1:50, preferably 1:1 to 1:20.

To enhance the selectivity for the product of the present invention, 4-nitroso-substituted aromatic amine, the nitroaromatic compound is slowly added to the amide compound used as a starting material for a predetermined time.

The mole ratio of the amide compound of the formula 4 to the nitroaromatic compound of the formula 3 is 1:1 to 1:30, preferably 1:1.5 to 1:6. The higher proportion of the amide compound increases the selectivity for 4-nitroso-substituted aromatic amine, while the higher proportion of the nitroaromatic compound not only increases the proportion of 4-nitro-substituted aromatic amine but also results in the product of the secondary reaction, 4,4'-dinitrodiphenylamine as a by-product. So the amount of the amide compound of the formula 4 is preferably in the above range.

Vacuum distillation or the use of a drying agent may be employed to eliminate water produced from the reaction solution in the early stage of the reaction or during the reaction. Specific examples of the drying agent available in the present invention may include anhydrous potassium carbonate, anhydrous sodium sulfate, anhydrous magnesium sulfate, sodium hydroxide, potassium hydroxide, sodium hydride, and molecular sieve. But the use of the drying agent or continuous distillation to remove water from the solution makes little difference in the yield of the product, because the amount of water hardly affects the reaction in the preparation method of the present invention.

The reaction temperature is properly in the range of 20 to 150° C., preferably 70 to 100° C. Temperature lower than 20° C. retards the rate of the reaction and deteriorates the selectivity for 4-nitroso-substituted aromatic amine, while temperature higher than 150° C. increases production of the by-product to deteriorate the yield of the product.

Nitrogen, oxygen or air is available as the reaction atmosphere in the present invention. The nitrogen atmosphere results in production of azoxybenzenes as a by-product, while the oxygen or air atmosphere suppresses production of azoxybenzenes and increases the yield of the product.

In the present invention, the products are analyzed and identified using NMR and GC-MSD measurements, and the reactants and the products are subjected to quantitative analysis using high performance liquid chromatography (hereinafter, referred to as "HPLC") under the following conditions. For HPLC, a Hitachi product composed of a L-6200 intelligent pump and a L-4200 UV-VIS detector is used with Cosmosil 5C18 (4.6×150 mm, packed column) for measurements at 254 nm, the development rate of the chromatographic eluant being 1 ml/min. The conditions of solvent gradient elution are presented in Table 1.

TABLE 1

| Solvent Gradient Elution Ratio | | |
|---|---|---|
| Time (min) | Solvent A % Purified water | Solvent B % Acetonitrile |
| 0 | 85 | 15 |
| 25 | 0 | 100 |
| 33 | 85 | 15 |

Pyrene is used as an internal standard material for determination of the product, and the area ratio for the concentration of each material based on the pyrene area is determined for standard calibration to calculate the molar concentration of the product from the calibration curve.

BEST MODE FOR CARRYING OUT THE INVENTION

Hereinafter, the present invention will be described in detail by way of the following examples, which are not intended to limit the scope of the present invention.

EXAMPLE 1

2.0 g (34 mmol) of acetamide, 4.1 g (68 mmol) of potassium hydroxide, 10 g of anhydrous potassium carbonate, 200 mg of pyrene and 15 ml of DMSO were added to a 100 ml reactor equipped with a condenser and a thermometer, and the mixture was heated with stirring in the oxygen atmosphere. As the reaction temperature reaches 85° C., 1.4 g (11 mmol) of nitrobenzene was added dropwise to the mixture through a dropping funnel for about 10 minutes. Extreme caution was used lest that the temperature in the reactor should exceed 85±4° C. The ending point of the reaction was determined using HPLC as the time that nitrobenzene disappeared. After 2 hours of reaction, DMSO was added to a predetermined amount of the reactant, diluted with ethylacetate and then analyzed with HPLC.

The conversion rate of nitrobenzene was 100%. According to the quantitative analysis, the yield of the products based on the internal standard material, pyrene was 61 mole % for 4-nitrosoaniline and 8 mol % for 4-nitroaniline.

$^1$H-NMR ([D$_6$] DMSO, 130° C.): 4-nitrosoaniline: 13.30 (s, 2H), 6.77(d, 2H, J=8.4 Hz), 7.61(d, 2H, J=8.4 Hz) (all signals were broad at the room temperature). m/z (Matrix: Glycerol, Ion mode: FAB$^+$): [M+1]$^+$=123.06

Comparative Example 1

This experiment was performed to identify the product according to the method disclosed in U.S. Pat. No. 5,331, 099. Contrary to the result of the present invention, the product was determined as an amide.

More specifically, 1.8 g (14 mmole) of TMA(OH).5H$_2$O as abase, 1.2 g (10 mmole) of benzamide and 10 ml of xylene were subjected to vacuum distillation under 740 mmHg/70° C. with stirring at 70° C. to distil water in the base with xylene and to remove it from the base. Then 1.2 g (10 mmole) of nitrobenzene was added dropwise. After 4 hours of reaction, an HPLC analysis showed that N-(4-nitrophenyl)benzamide was obtained with a yield of 98% based on benzamide.

EXAMPLE 2

This example shows the results of the use of different amides. Procedures were performed in the same manner as described in Example 1, excepting that various amides were used instead of acetamide as listed in Table 2. The results are presented in Table 2.

TABLE 2

| Amides | Conversion Rate (%) Nitrobenzene | Yield (mole %) | | | |
|---|---|---|---|---|---|
| | | 4-nitrosoaniline | 4-nitroaniline | N-(4-nitrophenyl)amide | Others |
| Acetamide | 100 | 61 | 8 | — | <1 |
| Formamide | 84 | 45 | 7 | — | 3 |
| Biuret | 97 | 43 | 10 | — | 3 |
| Benzamide | 100 | — | — | 98 (yield of N-(4-nitrophenyl)benzamide) | 2 |

EXAMPLE 3

Procedures were performed in the same manner as described in Example 1, excepting that the added amount of nitrobenzene based on acetamide was varied as listed in Table 3. The results are presented in Table 3.

TABLE 3

| Nitrobenzene/acetamide (mole ratio) | Conversion Rate (%) Nitrobenzene | Yield (mole %) | | |
|---|---|---|---|---|
| | | 4-nitrosoaniline | 4-nitroaniline | Others |
| 1/3 | 100 | 61 | 8 | <1 |
| 1/2 | 99 | 49 | 14 | 11 |
| 1 | 97 | 28 | 9 | 7 |

EXAMPLE 4

Procedures were performed in the same manner as described in Example 1, excepting that the type of the base was varied as listed in Table 4. The results are presented in Table 4.

TABLE 4

| Base | Conversion Rate (%) Nitrobenzene | Yield (mole %) | | |
|---|---|---|---|---|
| | | 4-nitrosoaniline | 4-nitroaniline | Others |
| KOH | 100 | 61 | 8 | <1 |
| TMA(OH) · 5H$_2$O | 100 | 63 | 6 | <1 |
| NaOH | 98 | 24 | 8 | 6 |
| t-BuOK | 99 | 15 | 7 | 8 |

EXAMPLE 5

This example relates to an experiment to determine the change in the yield of the product depending on the variation of the reaction temperature. Procedures were performed in the same manner as described in Example 1, excepting that the reaction temperature was varied as listed in Table 5. The results are presented in Table 5.

TABLE 5

| Reaction Temperature (° C.) | Conversion Rate (%) Nitrobenzene | Yield (mole %) | | |
|---|---|---|---|---|
| | | 4-nitroso-aniline | 4-nitro-aniline | Azoxybenzene |
| 50 | 57 | 19 | 7 | — |
| 70 | 99 | 58 | 11 | — |
| 85 | 100 | 61 | 8 | — |
| 100 | 100 | 35 | 1 | 2 |

EXAMPLE 6

Procedures were performed in the same manner as described in Example 1, excepting that the type of the solvent was varied as listed in Table 6. The results are presented in Table 6.

TABLE 6

| Solvent | Conversion Rate (%) Nitrobenzene | Yield (mole %) | | |
|---|---|---|---|---|
| | | 4-nitroso-aniline | 4-nitro-aniline | Others |
| DMSO | 100 | 61 | 8 | <1 |
| NMP | 95 | 6 | — | — |

EXAMPLE 7

Procedures were performed in the same manner as described in Example 1, excepting that the reaction system was in the nitrogen or air atmosphere. The results are presented in Table 7.

TABLE 7

| Gas | Conversion Rate (%) Nitrobenzene | Yield (mole %) | | |
|---|---|---|---|---|
| | | 4-nitrosoaniline | 4-nitroaniline | Azoxybenzene |
| $O_2$ | 100 | 61 | 8 | — |
| $N_2$ | 100 | 55 | 7 | 4 |

EXAMPLE 8

2.0 g (34 mmol) of acetamide, 4.1 g (68 mmol) of potassium hydroxide, 10 g of anhydrous potassium carbonate, 200 mg of pyrene and 15 ml of DMSO were added to a 100 ml reactor equipped with a condenser and a thermometer, and the mixture was heated with stirring in the oxygen atmosphere. As the reaction temperature reaches 85° C., 1.5 g (11 mmol) of 3-nitrotoluene was added dropwise to the mixture through a dropping funnel for about 10 minutes. Extreme caution was used lest that the temperature in the reactor should exceed 85±4° C.

After 2 hours of the reaction, post-treatment was performed as described in Example 1. According to a quantitative analysis, the conversion rate of 3-nitrotoluene was 75% and the yield of the individual product based on 3-nitrotolene was 46 mole % for 2-methyl-4-nitrosoaniline and 5 mol % for 2-methyl-4-nitroaniline (the HPLC correction value of 2-methyl-4-nitrosoaniline was that of 4-nitrosoaniline).

EXAMPLE 9

2.0 g (34 mmol) of acetamide, 4.1 g (68 mmol) of potassium hydroxide, 10 g of anhydrous potassium carbonate, 200 mg of pyrene and 15 ml of DMSO were added to a 100 ml reactor equipped with a condenser and a thermometer, and the mixture was heated with stirring in the oxygen atmosphere. As the reaction temperature reaches 85° C., 1.7 g (11 mmol) of 3-nitroanisole was added dropwise to the mixture through a dropping funnel for about 10 minutes. Extreme caution was used lest that the temperature in the reactor should exceed 85±4° C.

After 2 hours of the reaction, post-treatment was performed as described in Example 1. According to a quantitative analysis, the conversion rate of 3-nitroanisole was 100% and the yield of the individual product based on 3-nitroanisole was 29 mole % for 2-methoxy-4-nitrosoaniline and 14 mol % for 2-methoxy-4-nitroaniline (the HPLC correction value of 2-methoxy-4-nitrosoaniline was that of 4-nitrosoaniline).

INDUSTRIAL APPLICABILITY

As described above, the preparation method involving contacting an amide compound with a nitroaromatic compound in an appropriate condition produces 4-nitroso-substituted aromatic amine in one step without production of an intermediate, which method is economically preferable because it remarkably enhances the workability and provides a direct means for preparing as a major product 4-nitroso-substituted aromatic amine that is used as an intermediate for dyestuff and hair dyes and reduced to p-phenylene diamiene.

What is claimed is:

1. A method for preparing a 4-nitroso-substituted aromatic amine, the method comprising:

contacting a nitroaromatic compound represented by the following formula 3 with an amide compound represented by the following formula 4 in the presence of a base and a solvent to directly prepare a 4-nitroso-substituted aromatic amine represented by the following formula 1 as a main product and a 4-nitro-substituted aromatic amine represented by the following formula 2 as a byproduct in one step:

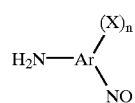

Formula 1 wherein Ar is a $C_4$ to $C_{16}$ aromatic group having at least one ring and containing one or two hetero atoms of N, O or S; X is a halogen atom, a cyano group, a $C_1$ to $C_4$ alkyl group, a halongenated $C_1$ to $C_4$ alkyl group, a $C_1$ to $C_4$ alkoxy group, a $C_1$ to $C_4$ halongenated alkoxy group, a $C_1$ to $C_4$ alkylsulfonyl group, or a $C_1$ to $C_4$ alkylnitro group; and n is an integer of 0 to 3, wherein Xs are different from one another when n is greater than 1;

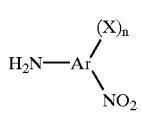

Formula 2 wherein Ar, X and n are as defined above;

Formula 3

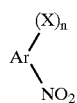

wherein Ar, X and n are as defined above; and

Formula 4

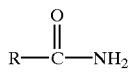

wherein R is a hydrogen atom, a $C_1$ to $C_8$ alkyl group, a $C_2$ to $C_8$ alkenyl group, or a $C_3$ to $C_7$ cycloalkyl group, which substituent may be replaced with 1 to 3 halogen atoms, $C_1$ to $C_4$ alkyl groups, amino groups or $C_1$ to $C_4$ alkoxy groups.

2. The method as claimed in claim 1, wherein the nitroaromatic compound of the formula 3 includes at least one selected from the group consisting of nitrobenzene, 2-nitrotoluene, 2-nitroanisole, 3-nitrotoluene and 3-nitroanisole.

3. The method as claimed in claim 1, wherein the amide compound of the formula 4 includes at least one selected from formamide, acetamide and biuret.

4. The method as claimed in claim 1, wherein the reaction is performed in the temperature range of 50 to 120° C.

5. The method as claimed in claim 1, wherein the solvent includes dimethylsulfoxide (DMSO) or N-methylpyrrolidinone (NMP) alone, or a mixed solvent of DMSO and an organic solvent.

6. The method as claimed in claim 1, wherein the base is any one selected from the group consisting of alkali metals including sodium hydroxide, sodium hydride, potassium hydroxide and potassium t-butoxy, or selected from inorganic bases used in combination with a phase transfer catalyst, and an organic base, tetramethylammonium hydroxide.

7. The method as claimed in claim 6, wherein the phase transfer catalyst used in combination with the inorganic bases includes tetramethylammonium chloride or 18-crown-6.

8. The method as claimed in claim 1, wherein the base is used at a mole ratio of 0.5 to 10 based on the amide compound of the formula 4.

9. The method as claimed in claim 1, wherein the mole ratio of the amide compound of the formula 4 to the nitroaromatic compound of the formula 3 is 1:1 to 1:30.

10. The method as claimed in claim 1, wherein the reaction is performed in the reaction atmosphere selected from the group consisting of nitrogen, oxygen, and air.

* * * * *